United States Patent
Bigorra Llosas et al.

(10) Patent No.: US 7,807,614 B2
(45) Date of Patent: Oct. 5, 2010

(54) QUATERNARY SURFACTANT CONCENTRATES

(75) Inventors: Joaquin Bigorra Llosas, Sabedell (ES); Karl Heinz Schmid, Mettmann (DE); Rafael Pi Subirana, Granollers (ES); Nuria Bonastre Gilabert, Barbera del Vall (ES)

(73) Assignee: Cognis IP Management GmbH, Duesseldorf (DE)

( * ) Notice: Subject to any disclaimer, the term of this patent is extended or adjusted under 35 U.S.C. 154(b) by 0 days.

(21) Appl. No.: 12/116,355

(22) Filed: May 7, 2008

(65) Prior Publication Data

US 2008/0207933 A1    Aug. 28, 2008

Related U.S. Application Data

(63) Continuation of application No. 10/472,668, filed as application No. PCT/EP02/02611 on Mar. 9, 2002, now abandoned.

(30) Foreign Application Priority Data

Mar. 20, 2001    (DE) ................. 101 13 334

(51) Int. Cl.
*C11D 1/90* (2006.01)
*C11D 1/62* (2006.01)

(52) U.S. Cl. .............. 510/490; 510/119; 510/124; 510/237; 510/350; 510/499; 510/501

(58) Field of Classification Search ........... 510/119, 510/124, 237, 350, 490, 499, 501
See application file for complete search history.

(56) References Cited

U.S. PATENT DOCUMENTS

| 3,225,074 | A | * | 12/1965 | Cowen et al. ............ 554/52 |
| 4,039,565 | A | * | 8/1977 | Throckmorton et al. ..... 558/28 |
| 4,136,054 | A | * | 1/1979 | Petzold et al. ......... 252/301.21 |
| 6,399,799 | B1 | * | 6/2002 | Pereira et al. ............ 554/52 |
| 2003/0130162 | A1 | * | 7/2003 | Llosas et al. ............. 510/515 |
| 2005/0123498 | A1 | * | 6/2005 | Pereira et al. .......... 424/70.28 |

* cited by examiner

*Primary Examiner*—Charles I Boyer

(57) ABSTRACT

Quaternary surfactants of the formula (I),

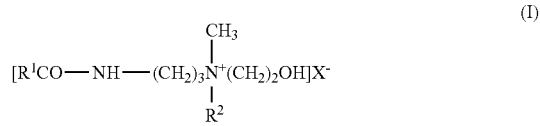

wherein $R^1CO$ is a linear or branched, saturated or unsaturated, optionally hydroxy-functionalized acyl radical having 6 to 22 carbon atoms and 0, 1, 2 or 3 double bonds, $R^2$ is a $CH_2COOH$ radical, an alkyl radical having 1 to 4 carbon atoms, a $CH_2CH_2OH$ or a $CH_2CH_2OCH_2CH_2OH$ group, and X is halide, alkyl sulfate, alkyl carbonate or alkyl phosphate, are useful as surfactants in cosmetic and pharmaceutical preparations. Aqueous solutions above 50% by weight of the surfactants are flowable and pumpable.

14 Claims, No Drawings

QUATERNARY SURFACTANT CONCENTRATES

CROSS-REFERENCE TO RELATED APPLICATIONS

This application is a continuation of application Ser. No. 10/472,668, filed on Sep. 22, 2003, now abandoned which was the national phase filing under 35 U.S.C. §371 of PCT International Application No. PCT/EP02/02611 which has an International filing date of Mar. 9, 2002, which designated the United States of America and which claims priority from German Patent Application number 101 13 334.0, filed Mar. 20, 2001, the entire contents of each of which are hereby incorporated herein by reference.

FIELD OF THE INVENTION

The invention is in the fields of cosmetics and detergents and relates to novel surfactants with a betaine or amide quat structure, to processes for the preparation thereof, and to their use for the preparation of surface-active compositions.

BACKGROUND INFORMATION

Surface-active substances with quaternary centers are divided roughly into amphoteric or zwitterionic surfactants on the one hand and cationic surfactants on the other hand. For both groups, there are countless examples in the market, such as, for example, the reaction products of fatty acid amidopropylamine with sodium chloroacetate (known under the INCI name Cocamidopropyl Betaine) or the alkylation products of triethanolamine fatty acid esters (known under the name ester quats). A common feature of these substances is their ability to attach to solid, especially negatively charged, surfaces, which is utilized, for example, for hand modifiers and hair-treatment compositions. Although the known products exhibit a performance which is in principle entirely satisfactory, there is still a desire for improved properties for a number of special applications. These include, in particular, the technically simple availability of concentrates with high storage stability.

Consequently, it was the object of the present invention to provide novel betaines or ester quats which, even at solids contents above 50% by weight, are flowable and pumpable, preferably have a Brookfield viscosity (20° C., spindle 1, 10 rpm) of less than 10 000 mPas and in particular less than 6 000 mPas. At the same time, the concentrates should neither gel nor change to a noteworthy degree with regard to their viscosity, even after storage at 40° C. for several weeks. Finally, it was desired to provide concentrates for various applications which are transparent even after prolonged storage under temperature. The demand for excellent biodegradability and dermatological compatibility represents a permanent requirement.

DESCRIPTION OF THE INVENTION

The invention provides quaternary surfactants of the formula (I),

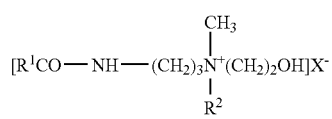

in which $R^1CO$ is a linear or branched, saturated or unsaturated, optionally hydroxy-functionalized acyl radical having 6 to 22 carbon atoms and 0, 1, 2 or 3 double bonds, $R^2$ is a $CH_2COOH$ radical or an alkyl radical having 1 to 4 carbon atoms, a $CH_2CH_2OH$ or $CH_2CH_2OCH_2CH_2OH$ group and X is halide, alkyl sulfate, alkyl carbonate or alkyl phosphate. The quaternary surfactants can here have either a betaine or amide quat structure, depending on the alkylating agent.

Surprisingly, it has been found that the novel surfactants can be adjusted to solids contents above 50% by weight without the addition of auxiliaries, such as, for example, (hydroxy)carboxylic acids, and nevertheless remain flowable and pumpable. In addition, even during storage under temperature, neither gelation nor collapse of the viscosity is observed. The concentrates are also transparent, particularly when dicarboxylic acids have been condensed into the molecule. The products are additionally completely biodegradable and are tolerated by the skin to an excellent degree.

The invention further provides a process for the preparation of quaternary surfactants of the formula (I),

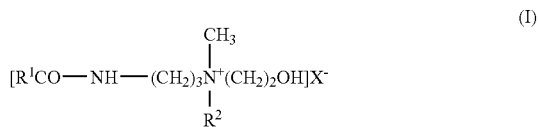

in which $R^1CO$ is a linear or branched, saturated or unsaturated, optionally hydroxy-functionalized acyl radical having 6 to 22 carbon atoms and 0, 1, 2 or 3 double bonds, $R^2$ is a $CH_2COOH$ radical or an alkyl radical having 1 to 4 carbon atoms, a $CH_2CH_2OH$ or $CH_2CH_2OCH_2CH_2OH$ group and X is halide, alkyl sulfate, alkyl carbonate or alkyl phosphate, which is characterized in that
(a) fatty acids and/or fatty acid glycerol esters are condensed with aminopropylmethylethanolamine, and
(b) the resulting fatty acid amidoamines are then quaternized with alkylating agents in a manner known per se.

Amidoamine Formation

Both for the betaines according to the invention and also for the amide quats, the amidoamines represent the common intermediates, which takes place either by amidation of the fatty acids or transamidation of the fatty acid glycerol esters, specifically the triglycerides, with aminopropylmethylethanolamine (APMEA). Suitable starting materials for the amidation are fatty acids of the formula (II)

in which $R^1CO$ has the meaning described above. Typical examples thereof are caproic acid, caprylic acid, 2-ethylhexanoic acid, capric acid, lauric acid, isotridecanoic acid, myristic acid, palmitic acid, palmoleic acid, stearic acid, isostearic acid, oleic acid, elaidic acid, petroselic acid, linoleic acid, linolenic acid, ricinoleic acid, 12-hydroxystearic acid, elaeostearic acid, arachidic acid, gadoleic acid, behenic acid, and erucic acid, and technical-grade mixtures thereof which are produced, for example, during the pressurized cleavage of natural fats and oils, during the reduction of aldehydes from the Roelen oxo synthesis or the dimerization of unsaturated fatty acids. Preference is given to technical-grade fatty acids having 12 to 18 carbon atoms, such as, for example, coconut, palm, palm kernel or tallow fatty acid. In place of the fatty acids, it is also possible for fatty acid glycerol esters which conform to the formula (III) to be transamidated:

Here, $R^1CO$ has the meaning given above, while $R^3$ and $R^4$, independently of one another, are hydrogen or optionally hydroxy-functionalized acyl radicals having 6 to 22 carbon atoms and 0, 1, 2 or 3 double bonds. Preferably, $R^3$ and $R^4$ are also acyl radicals, i.e. the fatty acid glycerol esters are natural or synthetic triglycerides, i.e. fats or oils, such as, for example, coconut oil, palm oil, palm kernel oil, olive oil, olive kernel oil, rapeseed oil, sunflower oil, groundnut oil, linseed oil, beef tallow or pork lard. It is likewise possible to carry out the condensation of the fatty acids or glycerides with the APMEA in the presence of defined amounts of dicarboxylic acids, such as, for example, oxalic acid, malonic acid, succinic acid, maleic acid, fumaric acid, glutaric acid, adipic acid, sorbic acid, pimelic acid, azelaic acid, sebacic acid and/or dodecanedioic acid. This method results in a partially oligomeric structure of the betaines or amide quats, which has a particularly advantageous effect on the solubility of the products to form clear solutions, particularly when adipic acid is co-used. Typically, the ratio of the free carboxylic acid groups between monocarboxylic acid and dicarboxylic acid is 90:10 to 80:20.

To prepare the fatty acid amidoamines, the fatty acids or fatty acid glycerol esters and the APMEA can be used in the molar ratio from 1.1:1 to 3:1. With regard to the performance properties of the resulting betaines or amide quats, a feed ratio of from 1.2:1 to 2.2:1, preferably 1.5:1 to 1.9:1, has proven particularly advantageous. The preferred fatty acid amidoamines are technical-grade mixtures of mono-, di- and triamides with an average degree of amidation of from 1.5 to 1.9. The condensation can be carried out in a manner known per se, i.e. in the presence of phosphorus or hypophosphorous acid as catalyst, and with removal of the water of condensation from the reaction equilibrium. Typically, the reaction is carried out at temperatures in the range from 150 to 200° C. over a period of from 2 to 8 h. For performance reasons, it is, moreover, advisable to remove free unreacted amine under reduced pressure in order that the intermediate is odorless and subsequent irritations are prevented.

Quaternization

The quaternization of the intermediates is an alkylation which leads to betaines or amide quats, depending on the alkylating agent. In the first case, suitable alkylating agents are chloroacetic acid and/or salts thereof, specifically sodium chloroacetate, and in the second case, suitable alkylating agents are alkyl halides, dialkyl sulfates, carbonates or phosphates, preferably methyl chloride, dimethyl sulfate or dimethyl carbonate. Alternatively, the quaternization can also be carried out with ethylene oxide. While the betainization is usually carried out in aqueous solution, the quaternization is usually carried out in alcoholic solution, preferably in ethanol, isopropyl alcohol or propylene glycol. The amount of quaternizing agent will usually be measured such that in all cases a small stoichiometric excess is present. Particularly when dimethyl sulfate is used, a small deficit is advisable in order to ensure that no traces of the alkylating agent remain in the end-product. In some cases, a thermal aftertreatment is advisable. The molar ratio of amidoamine to alkylating agent is therefore usually 1:0.95 to 1:1.05. The betainization or quaternization is usually carried out at temperatures in the range from 50 to 90° C. over a period of from 2 to 10 h.

INDUSTRIAL APPLICABILITY

The novel surfactants are characterized by typical amphoteric or cationic properties, i.e. attach to solid, especially negatively charged, surfaces. Further subject-matters of the invention therefore relate to their use for the preparation of cosmetic and/or pharmaceutical preparations, and also of laundry detergents, dishwashing detergents, cleaners and hand modifiers in which they may be present in amounts of from 1 to 30% by weight, preferably 5 to 25% by weight and in particular 10 to 15% by weight.

Cosmetic and/or Pharmaceutical Preparations

The surface-active preparations which comprise the novel surfactants are preferably skin- or hair-treatment compositions which can likewise have further auxiliaries and additives typical for these compositions. These include, for example, mild surfactants, oily bodies, emulsifiers, pearlescent waxes, bodying agents, thickeners, superfatting agents, stabilizers, polymers, silicone compounds, fats, waxes, lecithins, phospholipids, biogenic active ingredients, UV light protection factors, antioxidants, deodorants, antiperspirants, antidandruff agents, film formers, swelling agents, insect repellents, self-tanning agents, tyrosine inhibitors (depigmentation agents), hydrotropic agents, solubilizers, preservatives, perfume oils, dyes and the like.

Surfactants

Surface-active substances which may be present are anionic, nonionic, cationic and/or amphoteric or amphoteric surfactants, the content of which in the compositions is usually about 1 to 70% by weight, preferably 5 to 50% by weight and in particular 10 to 30% by weight. Typical examples of anionic surfactants are soaps, alkylbenzenesulfonates, alkanesulfonates, olefinsulfonates, alkyl ether sulfonates, glycerol ether sulfonates, α-methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids, such as, for example, acyl lactylates, acyl tartrates, acyl glutamates and acyl aspartates, alkyl oligoglucoside sulfates, protein fatty acid condensates (in particular wheat-based vegetable products) and alkyl (ether) phosphates. If the anionic surfactants contain polyglycol ether chains, these can have a conventional homolog distribution, but preferably have a narrowed homolog distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers or mixed formals, optionally partially oxidized alk(en)yl oligoglycosides or glucoronic acid derivatives, fatty acid N-alkylglucamides, protein hydrolysates (in particular wheat-based vegetable products), polyol fatty acid esters, sugar esters, sorbitan esters, polysorbates and amine oxides. If the nonionic surfactants contain polyglycol ether chains, these can have a conventional homolog distribution, but preferably have a narrowed homolog distribution. Typical examples of cationic surfactants are quaternary ammonium compounds, such as, for example, dimethyldistearylammonium chloride, and ester quats, in particular quaternized fatty acid trialkanolamine ester salts. Typical examples of amphoteric or zwitterionic surfactants are alkylbetaines, alkylamidobetaines, aminopropionates, aminoglycinates, imidazoliniumbetaines and sulfobetaines. Said surfactants are exclusively known compounds. With regard to structure and preparation of these substances, reference may be made to relevant review works, for example, J. Falbe (ed.), "Surfactants in Consumer Products", Springer Verlag, Berlin, 1987, pp. 54-124 or J. Falbe (ed.), "Katalysatoren, Tenside und Mineralöladditive", Thieme Verlag, Stuttgart, 1978, pp. 123-217. Typical examples of particularly suitable mild, i.e. particularly skin-compatible surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefin sulfonates, ether carboxylic acids, alkyl oligoglucosides, fatty acid glucamides, alkylamidobetaines, amphoacetals and/or protein fatty acid condensates, the latter preferably based on wheat proteins.

Oily Bodies

Suitable oily bodies are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols and/or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkyl hydroxycarboxylic acids with linear or branched $C_6$-$C_{22}$-fatty alcohols (cf. DE 19756377 A1), in particular dioctyl malates, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, dicaprylyl carbonate (Cetiol® CC), Guerbet carbonates based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or unsymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicon methicone types, inter alia) and/or aliphatic or naphthenic hydrocarbons, such as, for example, such as squalane, squalene or dialkylcyclohexanes under consideration.

Emulsifiers

Suitable emulsifiers are, for example, nonionogenic surfactants from at least one of the following groups;

addition products of from 2 to 30 mol of ethylene oxide and/or 0 to 5 mol of propylene oxide to linear fatty alcohols having 8 to 22 carbon atoms, to fatty acids having 12 to 22 carbon atoms, to alkylphenols having 8 to 15 carbon atoms in the alkyl group, and alkylamines having 8 to 22 carbon atoms in the alkyl radical;

alkyl and/or alkenyl oligoglycosides having 8 to 22 carbon atoms in the alk(en)yl radical and the ethoxylated analogs thereof;

addition products of from 1 to 15 mol of ethylene oxide to castor oil and/or hydrogenated castor oil;

addition products of from 15 to 60 mol of ethylene oxide to castor oil and/or hydrogenated castor oil;

partial esters of glycerol and/or sorbitan with unsaturated, linear or saturated, branched fatty acids having 12 to 22 carbon atoms and/or hydroxycarboxylic acids having 3 to 18 carbon atoms, and the adducts thereof with 1 to 30 mol of ethylene oxide;

partial esters of polyglycerol (average degree of self-condensation 2 to 8), polyethylene glycol (molecular weight 400 to 5 000), trimethylolpropane, pentaerythritol, sugar alcohols (e.g. sorbitol), alkyl glucosides (e.g. methyl glucoside, butyl glucoside, lauryl glucoside), and polyglucosides (e.g. cellulose) with saturated and/or unsaturated, linear or branched fatty acids having 12 to 22 carbon atoms and/or hydroxycarboxylic acids having 3 to 18 carbon atoms, and the adducts thereof with 1 to 30 mol of ethylene oxide;

mixed esters of pentaerythritol, fatty acids, citric acid and fatty alcohol as in German Patent 1165574 and/or mixed esters of fatty acids having 6 to 22 carbon atoms, methylglucose and polyols, preferably glycerol or polyglycerol, mono-, di- and trialkyl phosphates, and mono-, di- and/or tri-PEG alkyl phosphates and salts thereof;

wool wax alcohols;

polysiloxane-polyalkyl-polyether copolymers and corresponding derivatives;

block copolymers, e.g. polyethylene glycol-30 dipolyhydroxystearates;

polymer emulsifiers, e.g. Pemulen grades (TR-1, TR-2) from Goodrich;

polyalkylene glycols, and glycerol carbonate.

Ethylene Oxide Addition Products

The addition products of ethylene oxide and/or of propylene oxide to fatty alcohols, fatty acids, alkylphenols or to castor oil are known, commercially available products. These are homolog mixtures whose average degree of alkoxylation corresponds to the ratio of the amounts of substance of ethylene oxide and/or propylene oxide and substrate with which the addition reaction is carried out. $C_{12/18}$-fatty acid mono- and diesters of addition products of ethylene oxide to glycerol are known from German Patent 2024051 as refatting agents for cosmetic preparations.

Alkyl and/or Alkenyl Oligoglycosides

Alkyl and/or alkenyl oligoglycosides, their preparation and their use are known from the prior art. They are prepared, in particular, by reacting glucose or oligo-saccharides with primary alcohols having 8 to 18 carbon atoms. With regard to the glycoside radical, both monoglycosides, in which a cyclic sugar radical is glycosidically bonded to the fatty alcohol, and also oligomeric glycosides having a degree of oligomerization of up to, preferably, about 8, are suitable. The degree of oligomerization here is a statistical average value which is based on a homolog distribution customary for such technical-grade products.

Partial Glycerides

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride, and the technical-grade mixtures thereof which may also comprise small amounts of triglyceride as a minor product of the preparation process. Likewise suitable are addition products of 1 to 30 mol, preferably 5 to 10 mol, of ethylene oxide to said partial glycerides.

Sorbitan Esters

Sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate, and technical-grade mixtures thereof. Likewise suitable are addition products of from 1 to 30 mol, preferably 5 to 10 mol, of ethylene oxide to said sorbitan esters.

Polyglycerol Esters

Typical examples of suitable polyglycerol esters are polyglyceryl-2 dipolyhydroxystearate (Dehymuls® PGPH), polyglycerol-3 diisostearate (Lameform® TGI), polyglyceryl-4 isostearate (Isolan® GI 34), polyglyceryl-3 oleate, diisostearoyl polyglyceryl-3 diisostearate (Isolan® PDI), polyglyceryl-3 methylglucose distearate (Tego Care® 450), polyglyceryl-3 beeswax (Cera Bellina®), polyglyceryl-4 caprate (Polyglycerol Caprate T2010/90) polyglyceryl-3 cetyl ether (Chimexane® NL), polyglyceryl-3 distearate (Cremophor® GS 32) and polyglyceryl polyricinoleate (Admul® WOL 1403), polyglyceryl dimerate isostearate, and mixtures thereof. Examples of further suitable polyol esters are the mono-, di- and triesters, optionally reacted with 1 to 30 mol of ethylene oxide, of trimethylolpropane or pentaerythritol with lauric acid, coconut fatty acid, tallow fatty acid, palmitic acid, stearic acid, oleic acid, behenic acid and the like.

Anionic Emulsifiers

Typical anionic emulsifiers are aliphatic fatty acids having 12 to 22 carbon atoms, such as, for example, palmitic acid, stearic acid or behenic acid, and dicarboxylic acids having 12 to 22 carbon atoms, such as, for example, azelaic acid or sebacic acid.

Amphoteric and Cationic Emulsifiers

Furthermore, zwitterionic surfactants can be used as emulsifiers. The term "zwitterionic surfactants" refers to those surface-active compounds which carry at least one quaternary ammonium group and at least one carboxylate and one sulfonate group in the molecule. Particularly suitable zwitterionic surfactants are the so-called betaines, such as N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines having in each case 8 to 18 carbon atoms in the alkyl or acyl group, and cocoacylaminoethylhydroxyethylcarboxymethyl glycinate. Particular preference is given to the fatty acid amide derivative known under the CTFA name Cocamidopropyl Betaine. Likewise suitable emulsifiers are ampholytic surfactants. The term "ampholytic surfactants" means those surface-active compounds which, apart from a $C_{8/18}$-alkyl or -acyl group, contain at least one free amino group and at least one —COOH or —$SO_3H$ group in the molecule and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 18 carbon atoms in the alkyl group. Particularly preferred ampholytic surfactants are N-cocoalkylaminopropionate, cocoacylaminoethylaminopropionate and $C_{12/18}$-acylsarcosine. Finally, cationic surfactants are also suitable as emulsifiers, those of the ester quat type, preferably methyl-quaternized difatty acid triethanolamine ester salts, being particularly preferred.

Fats and Waxes

Typical examples of fats are glycerides, i.e. solid or liquid vegetable or animal products which consist essentially of mixed glycerol esters of higher fatty acids, suitable waxes are inter alia natural waxes, such as, for example, candelilla wax, carnauba wax, japan wax, esparto grass wax, cork wax, guaruma wax, rice germ oil wax, sugarcane wax, ouricury wax, montan wax, beeswax, shellac wax, spermaceti, lanolin (wool wax), uropygial grease, ceresin, ozokerite (earth wax), petrolatum, paraffin waxes, microcrystalline waxes; chemically modified waxes (hard waxes), such as, for example, montan ester waxes, sasol waxes, hydrogenated jojoba waxes, and synthetic waxes, such as, for example, polyalkylene waxes and polyethylene glycol waxes. In addition to the fats, suitable additives are also fat-like substances, such as lecithins and phospholipids. The term lecithins is understood by the person skilled in the art as meaning those glycerophospholipids which are founded from fatty acids, glycerol, phosphoric acid and choline by esterification. Lecithins are thus also often known as phosphatidylcholines (PC) in the specialist world. Examples of natural lecithins which may be mentioned are the cephalins, which are also referred to as phosphatidic acids, and derivatives of 1,2-diacyl-sn-glycerol-3-phosphoric acids. By contrast, phospholipids are usually understood as meaning mono- and preferably diesters of phosphoric acid with glycerol (glycerol phosphates), which are generally classed as fats. In addition, sphingosines or sphingolipids are also suitable.

Pearlescent Waxes

Examples of suitable pearlescent waxes are: alkylene glycol esters, specifically ethylene glycol distearate; fatty acid alkanolamides, specifically coconut fatty acid diethanolamide; partial glycerides, specifically stearic acid monoglyceride; esters of polybasic, optionally hydroxy-substituted carboxylic acids with fatty alcohols having 6 to 22 carbon atoms, specifically long-chain esters of tartaric acid; fatty substances, such as, for example, fatty alcohols, fatty ketones, fatty aldehydes, fatty ethers and fatty carbonates, which have a total of at least 24 carbon atoms, specifically laurone and distearyl ether; fatty acids, such as stearic acid, hydroxystearic acid or behenic acid, ring-opening products of olefin epoxides having 12 to 22 carbon atoms with fatty alcohols having 12 to 22 carbon atoms and/or polyols having 2 to 15 carbon atoms and 2 to 10 hydroxyl groups, and mixtures thereof.

Bodying Agents and Thickeners

Suitable bodying agents are primarily fatty alcohols or hydroxy fatty alcohols having 12 to 22, and preferably 16 to 18, carbon atoms, and also partial glycerides, fatty acids or hydroxy fatty acids. Preference is given to a combination of these substances with alkyl oligoglucosides and/or fatty acid N-methylglucamides of identical chain length and/or polyglycerol poly-12-hydroxystearates. Suitable thickeners are, for example, Aerosil grades (hydrophilic silicas), polysaccharides, in particular xanthan gum, guar guar, agar agar, alginates and Tyloses, carboxymethylcellulose, hydroxyethylcellulose and hydroxypropylcellulose, and also relatively high molecular weight polyethylene glycol mono- and diesters of fatty acids, polyacrylates (e.g. Carbopols® and Pemulen grades from Goodrich; Synthalens® from Sigma; Keltrol grades from Kelco; Sepigel grades from Seppic; Salcare grades from Allied Colloids), polyacrylamides, polymers, polyvinyl alcohol and polyvinylpyrrolidone. Bentonites, such as, for example, Bentone® Gel VS 5PC (Rheox), which is a mixture of cyclopentasiloxane, disteardimonium hectorite and propylene carbonate, have also proven to be particularly effective. Also suitable are surfactants, such as, for example, ethoxylated fatty acid glycerides, esters of fatty acids with polyols such as, for example, pentaerythritol or trimethylolpropane, fatty alcohol ethoxylates having a narrowed homolog distribution or alkyl oligoglucosides, and electrolytes such as sodium chloride and ammonium chloride.

Superfatting Agents

Superfatting agents which can be used are substances such as, for example, lanolin and lecithin, and polyethoxylated or acylated lanolin and lecithin derivatives, polyol fatty acid esters, monoglycerides and fatty acid alkanolamides, the latter also serving as foam stabilizers.

Stabilizers

Stabilizers which can be used are metal salts of fatty acids, such as, for example, magnesium, aluminum and/or zinc stearate or ricinoleate.

Polymers

Suitable cationic polymers are, for example, cationic cellulose derivatives, such as, for example, a quaternized hydroxyethylcellulose obtainable under the name Polymer JR 400® from Amerchol, cationic starch, copolymers of diallylammonium salts and acrylamides, quaternized vinylpyrrolidone-vinylimidazole polymers, such as, for example, Luviquat® (BASF), condensation products of polyglycols and amines, quaternized collagen polypeptides, such as, for example, lauryldimonium hydroxypropyl hydrolyzed collagen (Lamequat® L/Grünau), quaternized wheat polypeptides, polyethyleneimine, cationic silicone polymers, such as, for example, amodimethicones, copolymers of adipic acid and dimethylaminohydroxypropyldiethylenetriamine (Cartaretins®/Sandoz), copolymers of acrylic acid with dimethyldiallylammonium chloride (Merquat® 550/Chemviron), polyaminopolyamides, as described, for example, in FR 2252840 A, and crosslinked water-soluble polymers thereof, cationic chitin derivatives, such as, for example, quaternized chitosan, optionally in micro-crystalline dispersion, condensation products from dihaloalkyls, such as, for example, dibromobutane with bisdialkylamines, such as, for example, bis-dimethylamino-1,3-propane, cationic guar gum, such as, for example, Jaguar® CBS, Jaguar® C-17, Jaguar® C-16 from Celanese, quaternized ammonium salt polymers, such as, for example, Mirapol® A-15, Mirapol® AD-1, Mirapol® AZ-1 from Miranol.

Suitable anionic, zwitterionic, amphoteric and nonionic polymers are, for example, vinyl acetate-crotonic acid copolymers, vinylpyrrolidone-vinyl acrylate copolymers, vinyl acetate-butyl maleate-isobornyl acrylate copolymers, methyl vinyl ether-maleic anhydride copolymers and esters thereof, uncrosslinked polyacrylic acids and polyacrylic acids crosslinked with polyols, acrylamidopropyltrimethylammonium chloride-acrylate copolymers, octylacrylamide-methyl methacrylate-tert-butylaminoethyl methacrylate-2-hydroxypropyl methacrylate copolymers, polyvinylpyrrolidone, vinylpyrrolidone-vinyl acetate copolymers, vinylpyrrolidone-dimethylaminoethyl methacrylate-vinylcaprolactam terpolymers, and optionally derivatized cellulose ethers and silicones. Further suitable polymers and thickeners are listed in Cosm. Toil. 108, 95 (1993).

Silicone Compounds

Suitable silicone compounds are, for example, dimethylpolysiloxanes, methylphenylpolysiloxanes, cyclic silicones, and amino-, fatty acid-, alcohol-, polyether-, epoxy-, fluorine-, glycoside- and/or alkyl-modified silicone compounds, which can either be liquid or in resin form at room temperature. Also suitable are simethicones, which are mixtures of dimethicones having an average chain length of from 200 to 300 dimethylsiloxane units and hydrogenated silicates. A detailed review of suitable volatile silicones can additionally be found in Todd et al., Cosm. Toil. 91, 27 (1976).

UV Light Protection Filters and Antioxidants

UV light protection factors are, for example, to be understood as meaning organic substances (light protection filters) which are liquid or crystalline at room temperature and which are able to absorb ultraviolet rays and give off the absorbed energy again in the form of longer-wavelength radiation, e.g. heat. UVB filters can be oil-soluble or water-soluble. Examples of oil-soluble substances are:

- 3-benzylidenecamphor or 3-benzylidenenorcamphor and derivatives thereof, e.g. 3-(4-methylbenzylidene)camphor, as described in EP 0693471 B1;
- 4-aminobenzoic acid derivatives, preferably 2-ethylhexyl 4-(dimethylamino)benzoate, 2-octyl 4-(dimethylamino)benzoate and amyl 4-(dimethylamino)benzoate;
- esters of cinnamic acid, preferably 2-ethylhexyl 4-methoxycinnamate, propyl 4-methoxycinnamate, isoamyl 4-methoxycinnamate, 2-ethylhexyl 2-cyano-3,3-phenylcinnamate (octocrylene);
- esters of salicylic acid, preferably 2-ethylhexyl salicylate, 4-isopropylbenzyl salicylate, homomethyl salicylate;
- derivatives of benzophenone, preferably 2-hydroxy-4-methoxybenzophenone, 2-hydroxy-4-methoxy-4'-methylbenzophenone, 2,2'-dihydroxy-4-methoxybenzophenone;
- esters of benzalmalonic acid, preferably di-2-ethylhexyl 4-methoxybenzmalonate;
- triazine derivatives, such as, for example, 2,4,6-trianilino (p-carbo-2'-ethyl-1'-hexyloxy)-1,3,5-triazine and octyltriazone, as described in EP 0818450 A1 or dioctylbutamidotriazone (Uvasorb® HEB);
- propane-1,3-diones, such as, for example, 1-(4-tert-butylphenyl)-3-(4'-methoxyphenyl)propane-1,3-dione;
- ketotricyclo(5.2.1.0)decane derivatives, as described in EP 0694521 B1.

Suitable water-soluble substances are:

2-phenylbenzimidazole-5-sulfonic acid and the alkali metal, alkaline earth metal, ammonium, alkylammonium, alkanolammonium and glucammonium salts thereof;

sulfonic acid derivatives of benzophenones, preferably 2-hydroxy-4-methoxybenzophenone-5-sulfonic acid and its salts;

sulfonic acid derivatives of 3-benzylidenecamphor, such as, for example, 4-(2-oxo-3-bornylidenemethyl)benzenesulfonic acid and 2-methyl-5-(2-oxo-3-bornylidene) sulfonic acid and salts thereof.

Suitable typical UV-A filters are, in particular, derivatives of benzoylmethane, such as, for example, 1-(4'-tert-butylphenyl)-3-(4'-methoxyphenyl)propane-1,3-dione, 4-tert-butyl-4'-methoxydibenzoylmethane (Parsol® 1789), 1-phenyl-3-(4'-isopropylphenyl)propane-1,3-dione, and enamine compounds, as described in DE 19712033 A1 (BASF). The UV-A and UV-B filters can of course also be used in mixtures. Particularly favorable compositions consist of the derivatives of benzoylmethane e.g. 4-tert-butyl-4'-methoxydibenzoylmethane (Parsol® 1789) and 2-ethylhexyl 2-cyano-3,3-phenylcinnamate (octocrylene) in combination with esters of cinnamic acid, preferably 2-ethylhexyl 4-methoxycinnamate and/or propyl 4-methoxycinnamate and/or isoamyl 4-methoxycinnamate. Advantageously, such combinations are combined with water-soluble filters such as, for example, 2-phenylbenzimidazole-5-sulfonic acid and their alkali metal, alkaline earth metal, ammonium, alkylammonium, alkanolammonium and glucammonium salts.

As well as said soluble substances, insoluble light protection pigments, namely finely dispersed metal oxides or salts, are also suitable for this purpose. Examples of suitable metal oxides are, in particular, zinc oxide and titanium dioxide and also oxides of iron, zirconium, silicon, manganese, aluminum and cerium, and mixtures thereof. Salts which may be used are silicates (talc), barium sulfate or zinc stearate. The oxides and salts are used in the form of the pigments for skincare and skin-protective emulsions and decorative cosmetics. The particles here should have an average diameter of less than 100 nm, preferably between 5 and 50 nm and in particular between 15 and 30 nm. They can have a spherical shape, but it is also possible to use particles which have an ellipsoidal shape or a shape deviating in some other way from the spherical form. The pigments can also be surface-treated, i.e. hydrophilicized or hydrophobicized. Typical examples are coated titanium dioxides, such as, for example, titanium dioxide T 805 (Degussa) or Eusolex® T2000 (Merck). Suitable hydrophobic coating agents are here primarily silicones and, specifically in this case, trialkoxyoctylsilanes or simethicones. In sunscreens, preference is given to using so-called micro- or nanopigments. Preference is given to using micronized zinc oxide. Further suitable UV light protection filters are given in the review by P. Finkel in SÖFW-Journal 122, 543 (1996) and Parf. Kosm. 3, 11 (1999).

As well as the two abovementioned groups of primary light protection substances, it is also possible to use secondary light protection agents of the antioxidant type; these interrupt the photochemical reaction chain which is triggered when UV radiation penetrates the skin. Typical examples thereof are amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (e.g. buthionine sulfoximines, homocysteine sulfoximine, buthionine sulfones, penta-, hexa-, heptathionine sulfoximine) in very low tolerated doses (e.g. pmol to µmol/kg), and also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), and coniferyl benzoate of gum benzoin, rutic acid and derivatives thereof, α-glycosylrutin, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, superoxide dismutase, zinc and derivatives thereof (e.g. ZnO, $ZnSO_4$) selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) of said active ingredients which are suitable according to the invention.

Biogenic Active Ingredients

Biogenic active ingredients are understood as meaning, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, such as, for example, prunus extract, bambara nut extract and vitamin complexes.

Deodorants and Antimicrobial Agents

Cosmetic deodorants counteract, mask or remove body odors. Body odors arise as a result of the effect of skin bacteria on apocrine perspiration, with the formation of degradation products which have an unpleasant odor. Accordingly, deodorants comprise active ingredients which act as antimicrobial agents, enzyme inhibitors, odor absorbers or odor masking agents.

Antimicrobial Agents

Suitable antimicrobial agents are, in principle, all substances effective against gram-positive bacteria, such as, for example, 4-hydroxybenzoic acid and its salts and esters, N-(4-chlorophenyl)-N'-(3,4-dichlorophenyl)urea, 2,4,4'-trichloro-2'-hydroxydiphenyl ether (triclosan), 4-chloro-3,5-dimethylphenol, 2,2'-methylenebis(6-bromo-4-chlorophenol), 3-methyl-4-(1-methylethyl)phenol, 2-benzyl-4-chlorophenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, such as, for example, n-octylsalicylamide or n-decylsalicylamide.

Enzyme Inhibitors

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen® CAT). The substances inhibit enzyme activity, thereby reducing the formation of odor. Other substances which are suitable esterase inhibitors are sterol sulfates or phosphates, such as, for example, lanosterol, cholesterol, campesterol, stigmasterol and sitosterol sulfate or phosphate, dicarboxylic acids and esters thereof, such as, for example, glutaric acid, monoethyl glutarate, diethyl glutarate, adipic acid, monoethyl adipate, diethyl adipate, malonic acid and diethyl malonate, hydroxycarboxylic acids and esters thereof, such as, for example, citric acid, malic acid, tartaric acid or diethyl tartrate, and zinc glycinate.

Odor Absorbers

Suitable odor absorbers are substances which are able to absorb and largely retain odor-forming compounds. They lower the partial pressure of the individual components, thus also reducing their rate of diffusion. It is important that in this process perfumes must remain unimpaired. Odor absorbers are not effective against bacteria. They comprise, for example, as main constituent, a complex zinc salt of ricinoleic acid or specific, largely odor-neutral fragrances which are known to the person skilled in the art as "fixatives", such as, for example, extracts of labdanum or styrax or certain abietic acid derivatives. The odor masking agents are fragrances or perfume oils, which, in addition to their function as odor masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal raw materials, such as, for example, civet and castoreum. Typical synthetic fragrance compounds are products of the ester, ether, aldehyde, ketone, alcohol and hydrocarbon type. Fragrance compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether, and the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones and methyl cedryl ketone, the alcohols include anethole, citronellol, eugenol, isoeugenol, geraniol, linalool, phenylethyl alcohol and terpineol, and the hydrocarbons include mainly the terpenes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, melissa oil, mint oil, cinnamon leaf oil, linden blossom oil, juniper berry oil, vetiver oil, olibanum oil, galbanum oil, labdanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geraniol oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Antiperspirants

Antiperspirants reduce the formation of perspiration by influencing the activity of the eccrine sweat glands, thus counteracting underarm wetness and body odor. Aqueous or anhydrous formulations of antiperspirants typically comprise the following ingredients:

astringent active ingredients,
oil components,
nonionic emulsifiers,
coemulsifiers,
bodying agents,
auxiliaries, such as, for example, thickeners or complexing agents and/or
nonaqueous solvents, such as, for example, ethanol, propylene glycol and/or glycerol.

Suitable astringent antiperspirant active ingredients are primarily salts of aluminum, zirconium or of zinc. Such suitable antihydrotic active ingredients are, for example, aluminum chloride, aluminum chlorohydrate, aluminum dichlorohydrate, aluminum sesquichlorohydrate and complex compounds thereof, e.g. with 1,2-propylene glycol, aluminum hydroxyallantoinate, aluminum chloride tartrate, aluminum zirconium trichlorohydrate, aluminum zirconium tetrachlorohydrate, aluminum zirconium pentachlorohydrate and complex compounds thereof, e.g. with amino acids, such as glycine. In addition, customary oil-soluble and water-soluble auxiliaries may be present in antiperspirants in relatively small amounts. Such oil-soluble auxiliaries may, for example, be:

anti-inflammatory, skin-protective or perfumed essential oils,
synthetic skin-protective active ingredients and/or
oil-soluble perfume oils.

Customary water-soluble additives are, for example, preservatives, water-soluble fragrances, pH regulators, e.g. buffer mixtures, water-soluble thickeners, e.g. water-soluble natural or synthetic polymers, such as, for example, xanthan gum, hydroxyethylcellulose, polyvinylpyrrolidone or high molecular weight polyethylene oxides.

Film Formers

Customary film formers are, for example, chitosan, microcrystalline chitosan, quaternized chitosan, polyvinylpyrrolidone, vinylpyrrolidone-vinyl acetate copolymers, polymers of the acrylic acid series, quaternary cellulose derivatives, collagen, hyaluronic acid and salts thereof, and similar compounds.

Antidandruff Active Ingredients

Suitable antidandruff active ingredients are pirocton olamin (1-hydroxy-4-methyl-6-(2,4,4-trimythylpentyl)-2(1H)-pyridinone monoethanolamine salt), Baypival® (climbazole), Ketoconazole®, (4-acetyl-1-{-4-[2-(2,4-dichlorophenyl) r-2-(1H-imidazol-1-ylmethyl)-1,3-dioxylan-c-4-ylmethoxyphenyl}piperazine, ketoconazole, elubiol, selenium disulfide, sulfur colloidal, sulfur polyethylene glycol sorbitan monooleate, sulfur ricinole polyethoxylate, sulfur tar distillates, salicylic acid (or in combination with hexachlorophene) undexylenic acid monoethanolamide sulfosuccinate Na salt, Lamepon® UD (protein undecylenic acid condensate), zinc pyrithione, aluminum pyrithione and magnesium pyrithione/dipyrithione magnesium sulfate.

Swelling Agents

The swelling agents for aqueous phases may be montmorillonites, clay mineral substances, Pemulen, and alkyl-modified Carbopol grades (Goodrich). Other suitable polymers and swelling agents are given in the review by R. Lochhead in Cosm. Toil. 108, 95 (1993).

Insect Repellents

Suitable insect repellents are N,N-diethyl-m-toluamide, 1,2-pentanediol or ethyl butylacetylaminopropionate.

Self-Tanning Agents and Depigmentation Agents

A suitable self-tanning agent is dihydroxyacetone. Suitable tyrosine inhibitors, which prevent the formation of melanin and are used in depigmentation agents, are, for example, arbutin, ferulic acid, kojic acid, coumaric acid and ascorbic acid (vitamin C).

Hydrotropic Agents

To improve the flow behavior, it is also possible to use hydrotropic agents, such as, for example, ethanol, isopropyl alcohol, or polyols. Polyols which are suitable here preferably have 2 to 15 carbon atoms and at least two hydroxyl groups. The polyols can also contain further functional groups, in particular amino groups, or be modified with nitrogen. Typical examples are
- glycerol;
- alkylene glycols, such as, for example, ethylene glycol, diethylene glycol, propylene glycol, butylene glycol, hexylene glycol, and polyethylene glycols with an average molecular weight of from 100 to 1 000 daltons;
- technical-grade oligoglycerol mixtures with a degree of self-condensation of from 1.5 to 10, such as, for example, technical-grade diglycerol mixtures with a diglycerol content of from 40 to 50% by weight;
- methyol compounds, such as, in particular, trimethylolethane, trimethylolpropane, trimethylolbutane, pentaerythritol and dipentaerythritol;
- lower alkyl glucosides, in particular those having 1 to 8 carbon atoms in the alkyl radical, such as, for example, methyl and butyl glucoside;
- sugar alcohols having 5 to 12 carbon atoms, such as, for example, sorbitol or mannitol,
- sugars having 5 to 12 carbon atoms, such as, for example glucose or sucrose;
- amino sugars, such as, for example, glucamine;
- dialcohol amines, such as diethanolamine or 2-amino-1,3-propanediol.

Preservatives

Suitable preservatives are, for example, phenoxy ethanol, formaldehyde solution, parabenes, pentanediol or sorbic acid, and the silver complexes known under the name Surfacins®, and also the other classes of substance listed in Annex 6, Part A and B of the Cosmetics Directive.

Perfume Oils and Aromas

Perfume oils which may be mentioned are mixtures of natural and synthetic fragrances. Natural fragrances are extracts from flowers (lily, lavender, rose, jasmine, neroli, ylang-ylang), stems and leaves (geranium, patchouli, petitgrain), fruits (aniseed, coriander, cumin, juniper), fruit peels (bergamot, lemon, orange), roots (mace, angelica, celery, cardamon, costus, iris, calmus), woods (pinewood, sandalwood, guaiac wood, cedarwood, rosewood), herbs and grasses (tarragon, lemongrass, sage, thyme), needles and branches (spruce, fir, pine, dwarf-pine), resins and balsams (galbanum, elemi, benzoin, myrrh, olibanum, opoponax). Also suitable are animal raw materials, such as, for example, civet and castoreum. Typical synthetic fragrance compounds are products of the ester, ether, aldehyde, ketone, alcohol and hydrocarbon type. Fragrance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allyl cyclohexylpropionate, styrallyl propionate and benzyl salicylate. The ethers include, for example, benzyl ethyl ether, the aldehydes include, for example, the linear alkanals having 8 to 18 carbon atoms, citral, citronellal, citronellyloxyacetaldehyde, cyclamen aldehyde, hydroxycitronellal, lilial and bourgeonal, and the ketones include, for example, the ionones, α-isomethylionone and methyl cedryl ketone, the alcohols include anethole, citronellol, eugenol, isoeugenol, geraniol, linalool, phenylethyl alcohol and terpineol, and the hydrocarbons include mainly the terpenes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, melissa oil, mint oil, cinnamon leaf oil, linden blossom oil, juniper berry oil, vetiver oil, olibanum oil, galbanum oil, labolanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene torte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Suitable aromas are, for example, peppermint oil, spearmint oil, anise oil, star anise oil, caraway oil, eucalyptus oil, fennel oil, lemon oil, wintergreen oil, oil of cloves, menthol and the like.

Dyes

Dyes which can be used are the substances which are approved and suitable for cosmetic purposes, as are summarized, for example, in the publication "Kosmetische Färbemittel" [Cosmetic Colorants] from the Farbstoff-kommission der Deutechen Forschungsgemeinschaft [Dyes Commission of the German Research Council], Verlag Chemie, Weinheim, 1984, pp. 81-106. Examples are cochineal red A (C.I.16255), patent blue V (C.I.42051), indigotin (C.I.73015), chlorophyllin (C.I.75810), quinoline yellow (C.I.47005), titanium dioxide (C.I.77891), indanthrene blue RS (C.I.69800) and madder lake (C.I.58000). As a luminescent dye, it is also possible for luminol to be present. These dyes are customarily used in concentrations of from 0.001 to 0.1% by weight, based on the total mixture.

The total amount of auxiliaries and additives can be 1 to 50% by weight, preferably 5 to 40% by weight, based on the compositions. The compositions can be prepared by customary cold or hot processes; preference is given to using the phase-inversion temperature method.

Laundry Detergents, Dishwashing Detergents, Cleaners and Hand Modifiers

The surface-active compositions can, for example, also represent laundry detergents, dishwashing detergents, cleaners or hand modifiers which can further comprise auxiliaries and additives typical of these preparations. These include, for example, anionic, nonionic, cationic, amphoteric or zwitterionic surfactants, builders, cobuilders, oil- and grease-dissolving substances, bleaches, bleach activators, antiredeposition agents, enzymes, enzyme stabilizers, optical brighteners, polymers, defoamers, disintegrants, fragrances, inorganic salts and the like, as are explained in more detail below.

Anionic Surfactants

Typical examples of anionic surfactants are soaps, alkylbenzenesulfonates, alkanesulfonates, olefinsulfonates, alkyl ether sulfonates, glycerol ether sulfonates, α-methyl ester sulfonates, sulfo-fatty acids, alkyl sulfates, fatty alcohol ether sulfates, glycerol ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids, such as, for example, acyl lactylates, acyl tartrates, acyl glutamates and acyl aspartates, alkyl oligoglucoside sulfates, protein fatty acid condensates (in particular wheat-based vegetable products) and alkyl (ether) phosphates. If the anionic surfactants contain polyglycol ether chains, these can have a conventional homolog distribution, but preferably have a narrowed homolog distribution. Preference is given to using alkylbenzenesulfonates, alkyl sulfates, soaps, alkanesulfonates, olefinsulfonates, methyl ester sulfonates, and mixtures thereof. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers or mixed formals, alk(en)yl oligoglycosides, fatty acid N-alkylglucamides, protein hydrolysates (in particular wheat-based vegetable products), polyol fatty acid esters, sugar esters, sorbitan esters, polysorbates and amine oxides. If the nonionic surfactants contain polyglycol ether chains, these can have a conventional homolog distribution, but preferably have a narrowed homolog distribution. Preference is given to using fatty alcohol polyglycol ethers, alkoxylated fatty acid lower alkyl esters or alkyl oligoglucosides.

Builders

The laundry detergents, dishwashing detergents, cleaners and hand modifiers according to the invention can further comprise additional inorganic and organic builder substances, for example in amounts of from 10 to 50% by weight and preferably 15 to 35% by weight, based on the compositions, where the inorganic builder substances used are primarily zeolites, crystalline phyllosilicates, amorphous silicates and, where permissible, also phosphates, such as, for example, tripolyphosphate. The amount of cobuilder here is to be included in the preferred amounts of phosphates.

The finely crystalline, synthetic and bonded water-containing zeolite often used as detergent builder is preferably zeolite A and/or P. As zeolite P, particular preference is given, for example, to zeolite MAP® (commercial product from Crosfield). Also suitable, however, are zeolite X and mixtures of A, X and/or P and also Y. Of particular interest is also a cocrystallized sodium/potassium-aluminum silicate of zeolite A and zeolite X, which is available commercially as VEGOBOND AX® (commercial product from Condea Augusta S.p.A.). The zeolite can be used as a spray-dried powder or else as an undried stabilized suspension still moist from its preparation. In cases where the zeolite is used as suspension, the latter can comprise small additions of nonionic surfactants as stabilizers, for example 1 to 3% by weight, based on zeolite, of ethoxylated $C_{12}$-$C_{18}$-fatty alcohols having 2 to 5 ethylene oxide groups, $C_{12}$-$C_{14}$-fatty alcohols having 4 to 5 ethylene oxide groups or ethoxylated isotridecanols. Suitable zeolites have an average particle size of less than 10 μm (volume distribution; measurement method: Coulter counter) and preferably comprise 18 to 22% by weight, in particular 20 to 22% by weight, of bonded water.

Suitable substitutes or partial substitutes for phosphates and zeolites are crystalline, layered sodium silicates of the general formula $NaMSi_xO_{2x+1} \cdot yH_2O$, where M is sodium or hydrogen, x is a number from 1.9 to 4 and y is a number from 0 to 20 and preferred values for x are 2, 3 or 4. Such crystalline phyllosilicates are described, for example, in European patent application EP 0164514 A1. Preferred crystalline phyllosilicates of the given formula are those in which M is sodium and x assumes the values 2 or 3. Particular preference is given to both β- and also δ-sodium disilicates $Na_2Si_2O_5 \cdot yH_2O$, where β-sodium disilicate can be obtained, for example, by the process described in international patent application WO 91/08171. Further suitable phyllosilicates are known, for example, from the patent applications DE 2334899 A1, EP 0026529 A1 and DE 3526405 A1. Their usability is not limited to a specific composition or structural formula. Preference is given here, however, to smectites, in particular bentonites. Suitable phyllosilicates which belong to the group of water-swellable smectites are, for example, those of the general formulae

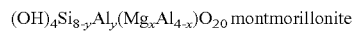

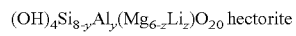

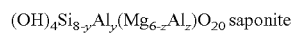

where x=0 to 4, y=0 to 2, z=0 to 6. In addition, small amounts of iron can be incorporated into the crystal lattice of the phyllosilicates according to the above formulae. In addition, the phyllosilicates can comprise hydrogen, alkali metal and alkaline earth metal ions, in particular $Na^+$ and $Ca^{2+}$, because of their ion-exchanging properties. The amount of water of hydration is in most cases in the range from 8 to 20% by weight and is dependent on the swelling state or on the type of processing. Phyllosilicates which can be used are, for example, known from U.S. Pat. Nos. 3,966,629, 4,062,647, EP 0026529 A1 and EP 0028432 A1. Preference is given to using phyllosilicates which, because of an alkali metal treatment, are largely free from calcium ions and strongly coloring iron ions.

Preferred builder substances also include amorphous sodium silicates with an $Na_2O:SiO_2$ modulus of from 1:2 to 1:3.3, preferably from 1:2 to 1:2.8 and in particular from 1:2 to 1:2.6, which have delayed dissolution and secondary detergency properties. The delayed dissolution compared with conventional amorphous sodium silicates can be brought about in a variety of ways, for example by surface treatment, compounding, compaction/compression or by overdrying. For the purposes of this invention, the term "amorphous", is also to be understood as meaning "X-ray-amorphous". This means that, in X-ray diffraction experiments, the silicates do not produce sharp X-ray reflections typical of crystalline substances, but, at best, one or more maxima of the scattered X-ray radiation having a breadth of several degree units of the diffraction angle. However, particularly good builder properties may very likely result if the silicate particles produce poorly defined or even sharp diffraction maxima in electron diffraction experiments. This is to be interpreted to the effect that the products have microcrystalline regions with a size from 10 to a few hundred nm, preference being given to values up to a maximum of 50 nm and in particular up to a maximum of 20 nm. Such so-called X-ray-amorphous silicates, which likewise have delayed dissolution compared with traditional waterglasses, are described, for example, in the German patent application DE 4400024 A1. Particular preference is given to compressed/compacted amorphous silicates, compounded amorphous silicates and overdried X-ray-amorphous silicates.

It is of course also possible to use the generally known phosphates as builder substances if such a use is not to be avoided for ecological reasons. Suitable are, in particular, the sodium salts of the orthophosphates, the pyrophosphates and, in particular, the tripolyphosphates. Their content is generally not more than 25% by weight, preferably not more than 20% by weight, in each case based on the finished composition. In some cases, it has been found that, in particular, tripolyphosphates, even in small amounts up to at most 10% by weight, based on the finished composition, in combination with other builder substances lead to a synergistic improvement in the secondary detergency.

Cobuilders

Organic framework substances which can be used and are suitable as cobuilders are, for example, the polycarboxylic acids which can be used in the form of their sodium salts, such as citric acid, adipic acid, succinic acid, glutaric acid, tartaric acid, sugar acids, aminocarboxylic acids, nitrilotriacetic acid (NTA), provided such a use is not objectionable for ecological reasons, and mixtures thereof. Preferred salts are the salts of the polycarboxylic acids, such as citric acid, adipic acid, succinic acid, glutaric acid, tartaric acid, sugar acids and mixtures thereof. The acids per se can also be used. In addition to their builder action, the acids typically also have the property of an acidifying component and thus also serve for setting a relatively low and relatively mild pH of laundry detergents or cleaners. In this connection, particular mention may be made of citric acid, succinic acid, glutaric acid, adipic acid, gluconic acid and any mixtures thereof.

Further suitable organic builder substances are dextrins, for example oligomers or polymers of carbohydrates which can be obtained by partial hydrolysis of starches. The hydrolysis can be carried out in accordance with customary, for example acid-catalyzed or enzyme-catalyzed, processes. The hydrolysis products preferably have average molar masses in the range from 400 to 500 000. Here, a polysaccharide with a dextrose equivalent (DE) in the range from 0.5 to 40, in particular from 2 to 30, is preferred, where DE is a usual measure of the reducing action of a polysaccharide compared with dextrose, which has a DE of 100. It is possible to use either maltodextrins with a DE between 3 and 20 and dry glucose syrups with a DE between 20 and 37, and also so-called yellow dextrins and white dextrins with relatively high molar masses in the range from 2 000 to 30 000. A preferred dextrin is described in British patent application GB 9419091 A1. The oxidized derivatives of such dextrins are their reaction products with oxidizing agents which are able to oxidize at least one alcohol function of the saccharide ring to give the carboxylic acid function. Such oxidized dextrins and processes for their preparation are known, for example, from European patent applications EP 0232202 A1, EP 0427349 A1, EP 0472042 A1 and EP 0542496 A1, and the international patent applications WO 92/18542, WO 93/08251, WO 93/16110, WO 94/28030, WO 95/07303, WO 95/12619 and WO 95/20608. Also suitable is an oxidized oligosaccharide according to German patent application DE 19600018 A1. A product oxidized on $C_6$ of the saccharide ring may be particularly advantageous.

Further suitable co-builders are oxydisuccinates and other derivatives of disuccinates, preferably ethylenediamine disuccinate. Particular preference is also given in this connection to glycerol disuccinates and glycerol trisuccinates, as are described, for example, in US-American patent specifications U.S. Pat. Nos. 4,524,009, 4,639,325, in the European patent application EP 0150930 A1 and the Japanese patent application JP 93/339896. Suitable use amounts in zeolite-containing and/or silicate-containing formulations are 3 to 15% by weight. Further organic co-builders which can be used are, for example, acetylated hydroxycarboxylic acids or salts thereof, which may optionally also be in lactone form and which contain at least 4 carbon atoms and at least one hydroxyl group and a maximum of two acid groups. Such co-builders are described, for example, in international patent application WO 95/20029.

Suitable polymeric polycarboxylates are, for example, the sodium salts of polyacrylic acid or of polymethacrylic acid, for example those with a relative molecular mass of from 800 to 150 000 (based on acid and in each case measured against polystyrenesulfonic acid). Suitable copolymeric polycarboxylates are, in particular, those of acrylic acid with methacrylic acid and of acrylic acid or methacrylic acid with maleic acid. Copolymers of acrylic acid with maleic acid which contain 50 to 90% by weight of acrylic acid and 50 to 10% by weight of maleic acid have proven particularly suitable. Their relative molecular mass, based on free acids, is generally 5 000 to 200 000, preferably 10 000 to 120 000 and in particular 50 000 to 100 000 (in each case measured against polystyrenesulfonic acid). The (co)polymeric polycarboxylates can either be used as powder or as aqueous solution, preference being given to 20 to 55% by weight strength aqueous solutions. Granular polymers are in most cases added subsequently to one or more base granulates. Particular preference is also given to biodegradable polymers of more than two different monomer units, for example those which, according to DE 4300772 A1, contain salts of acrylic acid and of maleic acid and vinyl alcohol or vinyl alcohol derivatives as monomers, or, according to DE 4221381 C2, salts of acrylic acid and of 2-alkylallylsulfonic acid and sugar derivatives as monomers. Further preferred copolymers are those which are described in German patent applications DE 4303320 A1 and DE 4417734 A1 and have, as monomers, preferably acrolein and acrylic acid/acrylic acid salts or acrolein and vinyl acetate. Further preferred builder substances are also polymeric aminodicarboxylic acids, salts thereof or precursor substances thereof. Particular preference is given to polyaspartic acids or salts and derivatives thereof.

Further suitable builder substances are polyacetals, which can be obtained by reacting dialdehydes with polyolcarboxylic acids which have 5 to 7 carbon atoms and at least 3 hydroxyl groups, for example as described in European patent application EP 0280223 A1. Preferred polyacetals are obtained from dialdehydes such as glyoxal, glutaraldehyde, terephthalaldehyde and mixtures thereof and from polyolcarboxylic acids such as gluconic acid and/or glucoheptonic acid.

Oil- and Grease-dissolving Substances

In addition, the compositions can also comprise components which have a positive effect on the ability to wash oil and grease out of textiles. Preferred oil- and grease-dissolving components include, for example, nonionic cellulose ethers, such as methylcellulose and methylhydroxypropylcellulose having a proportion of methoxy groups of from 15 to 30% by weight and of hydroxypropoxy groups of from 1 to 15% by weight, in each case based on the nonionic cellulose ethers, and the polymers, known from the prior art, of phthalic acid and/or of terephthalic acid, or of derivatives thereof, in particular polymers of ethylene terephthalates and/or polyethylene glycol terephthalates or anionically and/or nonionically modified derivatives thereof. Of these, particular preference is given to the sulfonated derivatives of phthalic acid polymers and of terephthalic acid polymers.

Bleaches and Bleach Activators

Among the compounds which supply $H_2O_2$ in water and which serve as bleaches, sodium perborate tetrahydrate and sodium perborate monohydrate are of particular importance. Further bleaches which can be used are, for example, sodium percarbonate, peroxypyrophosphates, citrate perhydrates, and $H_2O_2$-supplying peracidic salts or peracids, such as perbenzoates, peroxophthalates, diperazelaic acid, phthaloimino peracid or diperdodecanedioic acid. The content of bleaches in the compositions is preferably 5 to 35% by weight and in particular up to 30% by weight, where perborate monohydrate or percarbonate is used advantageously.

Bleach activators which can be used are compounds which, under perhydrolysis conditions, produce aliphatic peroxocarboxylic acids having, preferably, 1 to 10 carbon atoms, in particular 2 to 4 carbon atoms, and/or optionally substituted perbenzoic acid. Substances which carry O- and/or N-acyl groups of said number of carbon atoms and/or optionally substituted benzoyl groups are suitable. Preference is given to polyacylated alkylenediamines, in particular tetraacetylethylenediamine (TAED), acylated triazine derivatives, in particular 1,5-diacetyl-2,4-dioxohexahydro-1,3,5-triazine (DADHT), acylated glycolurils, in particular tetraacetylglycoluril (TAGU), N-acylimides, in particular N-nonanoylsuccinimide (NOSI), acylated phenolsulfonates, in particular n-nonanoyl- or isononanoyl-oxybenzenesulfonate (n- or iso-NOBS), carboxylic anhydrides, in particular phthalic anhydride, acylated polyhydric alcohols, in particular triacetin, ethylene glycol diacetate, 2,5-diacetoxy-2,5-dihydrofuran and the enol esters known from German patent applications DE 19616693 A1 and DE 19616767 A1, and acetylated sorbitol and mannitol or mixtures thereof described in European patent application EP 0525239 A1 (SORMAN), acylated sugar derivatives, in particular pentaacetylglucose (PAG), pentaacetylfructose, tetraacetylxylose and octaacetyllactose, and acetylated, optionally N-alkylated glucamine and gluconolactone, and/or N-acylated lactams, for example N-benzoylcaprolactam, which are known from international patent applications WO 94/27970, WO 94/28102, WO 94/28103, WO 95/00626, WO 95/14759 and WO 95/17498. The hydrophilically substituted acylacetals known from German patent application DE 19616769 A1, and the acyllactams described in German patent application DE 196 16 770 and international patent application WO 95/14075 are likewise used with preference. The combinations of conventional bleach activators known from German patent application DE 4443177 A1 can also be used. Such bleach activators are present in the customary quantitative range, preferably in amounts of from 1% by weight to 10% by weight, in particular 2% by weight to 8% by weight, based on the overall composition. In addition to the above-listed conventional bleach activators, or instead of them, the sulfonimines known from European patent specifications EP 0446982 B1 and EP 0453 003 B1 and/or bleach-boosting transition metal salts or transition metal complexes may also be present as so-called bleach catalysts. Suitable transition metal compounds include, in particular, the manganese-, iron-, cobalt-, ruthenium- or molybdenum-salen complexes known from German patent application DE 19529905 A1, and their N-analogous compounds known from German patent application DE 19620267 A1, the manganese-, iron-, cobalt-, ruthenium- or molybdenum-carbonyl complexes known from German patent application DE 19536082 A1, the manganese, iron, cobalt, ruthenium, molybdenum, titanium, vanadium and copper complexes having nitrogen-containing tripod ligands described in German patent application DE 19605688 A1, the cobalt-, iron-, copper- and ruthenium-amine complexes known from German patent application DE 19620411 A1, the manganese, copper and cobalt complexes described in German patent application DE 4416438 A1, the cobalt complexes described in European patent application EP 0272030 A1, the manganese complexes known from European patent application EP 0693550 A1, the manganese, iron, cobalt and copper complexes known from European patent specification EP 0392592 A1, and/or the manganese complexes described in European patent specification EP 0443651 B1 or European patent applications EP 0458397 A1, EP 0458398 A1, EP 0549271 A1, EP 0549272 A1, EP 0544490 A1 and EP 0544519 A1. Combinations of bleach activators and transition metal bleach catalysts are known, for example, from German patent application DE 19613103 A1 and international patent application WO 95/27775. Bleach-boosting transition metal complexes, in particular with the central atoms Mn, Fe, Co, Cu, Mo, V, Ti and/or Ru, are used in customary amounts, preferably in an amount up to 1% by weight, in particular from 0.0025% by weight to 0.25% by weight and particularly preferably from 0.01% by weight to 0.1% by weight, in each case based on the overall composition.

Enzymes and Enzyme Stabilizers

Suitable enzymes are, in particular, those from the class of hydrolases, such as proteases, esterases, lipases or lipolytic enzymes, amylases, cellulases or other glycosylhydrolases and mixtures of said enzymes. All of these hydrolases contribute during washing to the removal of stains, such as protein, grease or starchy stains, and redeposition. Cellulases and other glycosyl hydrolases may, by removing pilling and microfibrils, contribute to color retention and to an increase in the softness of the textile. For bleaching or for inhibiting color transfer, it is also possible to use oxidoreductases. Particularly suitable enzymatic active ingredients are those obtained from bacterial strains or fungi, such as *Bacillus subtilis, Bacillus licheniformis, Streptomyces griseus* and *Humicola insolens*. Preference is given to using proteases of the subtilisin type and, in particular, proteases obtained from *Bacillus lentus*. Of particular interest in this connection are enzyme mixtures, for example mixtures of protease and amylase or protease and lipase or lipolytic enzymes, or protease and cellulase or of cellulase and lipase or lipolytic enzymes or of protease, amylase and lipase or lipolytic enzymes or protease, lipase or lipolytic enzymes and cellulase, in particular, however, protease- and/or lipase-containing mixtures or mixtures containing lipolytic enzymes. Examples of such lipolytic enzymes are the known cutinases. Peroxidases or oxidases have also proven suitable in some cases. Suitable amylases include, in particular, α-amylases, isoamylases, pullulanases and pectinases. The cellulases used are preferably cellobiohydrolases, endoglucanases and β-glucosidases, which are also called cellobiases, or mixtures thereof, Since the various cellulase types differ in their CMCase and avicelase activities, it is possible to adjust the desired activities through targeted mixing of the cellulases.

The enzymes for their part can also be adsorbed on carrier substances and/or embedded in coating substances in order to protect them against premature decomposition. The proportion of enzymes, enzyme mixtures or enzyme granulates can, for example, be from about 0.1 to 5% by weight, preferably 0.1 to about 2% by weight.

In addition to the mono- and polyfunctional alcohols, the compositions can comprise further enzyme stabilizers. For example, 0.5 to 1% by weight of sodium formate can be used. The use of proteases which have been stabilized with soluble calcium salts and a calcium content of, preferably, about 1.2% by weight, based on the enzyme, is also possible. Apart from calcium salts, magnesium salts also serve as stabilizers. However, the use of boron compounds, for example of boric acid, boron oxide, borax and other alkali metal borates, such as the salts of orthoboric acid ($H_3BO_3$), of metaboric acid ($HBO_2$) and of pyroboric acid (tetraboric acid $H_2B_4O_7$) is particularly advantageous.

Antiredeposition Agents

Antiredeposition agents have the task of keeping the soil detached from the fiber in suspended form in the liquor, and thus preventing reattachment of the soil. For this purpose, water-soluble colloids of a mostly organic nature are suitable, for example the water-soluble salts of polymeric carboxylic acids, glue, gelatin, salts of ether carboxylic acids or ether sulfonic acids of starch or of cellulose or salts of acidic sulfuric esters of cellulose or of starch. Water-soluble polyamides which contain acidic groups are also suitable for this purpose. In addition, it is also possible to use soluble starch preparations, and starch products other than those mentioned above, e.g. degraded starch, aldehyde starches etc. Polyvinylpyrrolidone can also be used. Preference is, however, given to using cellulose ethers, such as carboxymethylcellulose (Na salt), methylcellulose, hydroxyalkylcellulose and mixed ethers, such as methylhydroxyethylcellulose, methylhydroxypropylcellulose, methylcarboxymethylcellulose and mixtures thereof, and polyvinylpyrrolidone, for example in amounts of from 0.1 to 5% by weight, based on the compositions.

Optical Brighteners

The compositions can comprise derivatives of diaminostilbenedisulfonic acid, or alkali metal salts thereof, as optical brighteners. For example, salts of 4,4'-bis(2-anilino-4-morpholino-1,3,5-triazinyl-6-amino) stilbene-2,2'-disulfonic acid or compounds constructed in a similar way which carry a diethanolamino group, a methylamino group, an anilino group or a 2-methoxyethylamino group instead of the morpholino group are suitable. Brighteners of the substituted diphenylstyryl type may also be present, e.g. the alkali metal salts of 4,4'-bis(2-sulfostyryl)diphenyl, 4,4'-bis(4-chloro-3-sulfostyryl)-diphenyl, or 4-(4-chlorostyryl)-4'-(2-sulfostyryl)diphenyl. Mixtures of the above-mentioned brighteners may also be used. Uniformly white granulates are obtained if the compositions comprise, in addition to the customary brighteners in customary amounts, for example between 0.1 and 0.5% by weight, preferably between 0.1 and 0.3% by weight, also small amounts, for example $10^{-6}$ to $10^{-3}$% by weight, preferably around $10^{-5}$% by weight, of a blue dye. A particularly preferred dye is Tinolux® (commercial product from Ciba-Geigy).

Polymers

Suitable soil-repellent polymers are those which preferably contain ethylene terephthalate and/or polyethylene glycol terephthalate groups, where the molar ratio of ethylene terephthalate to polyethylene glycol terephthalate may be in the range from 50:50 to 90:10. The molecular weight of the linking polyethylene glycol units is, in particular, in the range from 750 to 5000, i.e. the degree of ethoxylation of the polyethylene glycol group-containing polymers may be about 15 to 100. The polymers are characterized by an average molecular weight of about 5000 to 200 000 and can have a block structure, but preferably have a random structure. Preferred polymers are those with ethylene terephthalate/polyethylene glycol terephthalate molar ratios of from about 65:35 to about 90:10, preferably from about 70:30 to 80:20. Also preferred are those polymers which have linking polyethylene glycol units with a molecular weight of from 750 to 5 000, preferably from 1 000 to about 3 000 and a molecular weight of the polymer from about 10 000 to about 50 000. Examples of commercially available polymers are the products Milease® T (ICI) or Repelotex® SRP 3 (Rhône-Poulenc).

Defoamers

Defoamers which can be used are wax-like compounds. "Wax-like" is to be understood as meaning those compounds which have a melting point at atmospheric pressure above 25° C. (room temperature), preferably above 50° C. and in particular above 70° C. The wax-like defoamer substances are virtually insoluble in water, i.e. at 20° C. they have a solubility below 0.1 by weight in 100 g of water. In principle, all wax-like defoamer substances known from the prior art may be present. Suitable wax-like compounds are, for example, bisamides, fatty alcohols, fatty acids, carboxylic esters of mono- and polyhydric alcohols, and paraffin waxes or mixtures thereof. Alternatively, the silicone compounds known for this purpose can of course also be used.

Suitable paraffin waxes are generally a complex mixture of substances without a sharp melting point. For characterization, its melting range is usually determined by differential thermoanalysis (DTA), as described in "The Analyst," 87 (1962), 420, and/or its solidification point. This is to be understood as meaning the temperature at which the paraffin converts from the liquid state to the solid state by slow cooling. Here, paraffins which are entirely liquid at room temperature, i.e. those with a solidification point below 25° C., cannot be used according to the invention. The soft waxes, which have a melting point in the range from 35 to 50° C. preferably include the group of petrolatums and hydrogenation products thereof. They are composed of microcrystalline paraffins and up to 70% by weight of oil, have an ointment-like to plastically solid consistency and represent bitumen-free residues from petroleum refining. Particular preference is given to distillation residues (petrolatum stock) of certain paraffin-base and mixed-base crude oils which are further processed to give vaseline. Preferably, they are also bitumen-free, oil-like to solid hydrocarbons deposited from distillation residues of paraffin-base and mixed-base crude oils and cylinder oil distillates by means of solvents. They are of semisolid, viscous, tacky or plastically solid consistency and have melting points between 50 and 70° C. These petrolatums represent the most important starting base for the preparation of microcrystalline waxes. Also suitable are the solid hydrocarbons having melting points between 63 and 79° C. deposited from high-viscosity, paraffin-containing lubricating oil distillates during deparaffinization. These petrolatums are mixtures of microcrystalline waxes and high-melting n-paraffins. It is possible to use, for example, the paraffin wax mixtures known from EP 0309931 A1 which are composed of, for example, 26% by weight to 49% by weight of microcrystalline paraffin wax with a solidification point of 62° C. to 90° C., 20% by weight to 49% by weight of hard paraffin with a solidification point of 42° C. to 56° C. and 2% by weight to 25% by weight of soft paraffin with a solidification point of from 35° C. to 40° C. Preference is given to using paraffins or paraffin mixtures which solidify in the range from 30° C. to 90° C. In this connection, it is to be taken into consideration that even paraffin wax mixtures which appear to be solid at room temperature may also comprise varying proportions of liquid paraffin. In the case of the paraffin waxes which can be used according to the invention, this liquid proportion is as low as possible and is preferably not present at all. Thus, particularly preferred paraffin wax mixtures have at 30° C. a liquid content of less than 10% by weight, in particular of from 2% by weight to 5% by weight, at 40° C. a liquid content of less than 30% by weight, preferably of from 5% by weight to 25% by weight and in particular from 5% by weight to 15% by weight, at 60° C. a liquid content of from 30% by weight to 60% by weight, in particular from 40% by weight to 55% by weight, at 80° C. a liquid content of from 80% by weight to 100% by weight and at 90° C. a liquid content of 100% by weight. The temperature at which a liquid content of 100% by weight of the paraffin wax is achieved is, in the case of particularly preferred paraffin wax mixtures, still below 85° C., in particular 75° C. to 82° C. The paraffin waxes may be petrolatum, microcrystalline waxes or hydrogenated or partially hydrogenated paraffin waxes.

Suitable bisamides as defoamers are those which are derived from saturated fatty acids having 12 to 22, preferably 14 to 18, carbon atoms, and from alkylenediamines having 2 to 7 carbon atoms. Suitable fatty acids are lauric acid, myristic acid, stearic acid, arachidic acid and behenic acid, and mixtures thereof, as are obtainable from natural fats or hydrogenated oils, such as tallow or hydrogenated palm oil. Suitable diamines are, for example, ethylenediamine, 1,3-propylenediamine, tetramethylenediamine, pentamethylenediamine, hexamethylenediamine, p-phenylenediamine and tolylenediamine. Preferred diamines are ethylenediamine and hexamethylenediamine. Particularly preferred bisamides are bis-myristoylethylenediamine, bispalmitoylethylenediamine, bis-stearoylethylenediamine and mixtures thereof, and the corresponding derivatives of hexamethylenediamine.

Suitable carboxylic esters as defoamers are derived from carboxylic acids having 12 to 28 carbon atoms. In particular, these are esters of behenic acid, stearic acid, hydroxystearic acid, oleic acid, palmitic acid, myristic acid and/or lauric acid. The alcohol moiety of the carboxylic ester comprises a mono- or polyhydric alcohol having from 1 to 28 carbon atoms in the hydro-carbon chain. Examples of suitable alcohols are behenyl alcohol, arachidyl alcohol, cocoyl alcohol, 12-hydroxy-stearyl alcohol, oleyl alcohol and lauryl alcohol, and also ethylene glycol, glycerol, polyvinyl alcohol, sucrose, erythritol, pentaerythritol, sorbitan and/or sorbitol. Preferred esters are those of ethylene glycol, glycerol and sorbitan, where the acid moiety of the ester is, in particular, chosen from behenic acid, stearic acid, oleic acid, palmitic acid or myristic acid. Suitable esters of polyhydric alcohols are, for example, xylitol monopalmitate, pentaerythritol monostearate, glycerol monostearate, ethylene glycol monostearate and sorbitan monostearate, sorbitan palmitate, sorbitan monolaurate, sorbitan dilaurate, sorbitan distearate, sorbitan dibehenate, sorbitan dioleate, and mixed tallow alkyl sorbitan monoesters and diesters. Glycerol esters which can be used are the mono-, di- or triesters of glycerol and said carboxylic acids, preference being given to the mono- or diesters. Glycerol monostearate, glycerol monooleate, glycerol monopalmitate, glycerol monobehenate and glycerol distearate are examples thereof. Examples of suitable natural esters as defoamers are beeswax, which consists primarily of the esters $CH_3(CH_2)_{24}COO(CH_2)_{27}CH_3$ and $CH_3(CH_2)_{26}COO(CH_2)_{25}CH_3$, and carnauba wax, which is a mixture of carnaubic acid alkyl esters, often in combination with small amounts of free carnaubic acid, further long-chain acids, high molecular weight alcohols and hydrocarbons.

Suitable carboxylic acids as further defoamer compound are, in particular, behenic acid, stearic acid, oleic acid, palmitic acid, myristic acid and lauric acid, and mixtures thereof as are obtainable from natural fats or optionally hydrogenated oils, such as tallow or hydrogenated palm oil. Preference is given to saturated fatty acids having 12 to 22, in particular 18 to 22, carbon atoms. The corresponding fatty alcohols of the same carbon chain length may likewise be used.

In addition, dialkyl ethers may additionally be present as defoamers. The ethers may have an asymmetrical or symmetrical structure, i.e. contain two identical or different alkyl chains, preferably having 8 to 18 carbon atoms. Typical examples are di-n-octyl ether, di-isooctyl ether and di-n-stearyl ether. Dialkyl ethers which have a melting point above 25° C., in particular above 40° C. are particularly suitable.

Further suitable defoamer compounds are fatty ketones, which can be obtained in accordance with the relevant methods of preparative organic chemistry. They are prepared, for example, starting from carboxylic acid magnesium salts, which are pyrolyzed at temperatures above 300° C. with elimination of carbon dioxide and water, for example in accordance with German laid-open specification DE 2553900 A. Suitable fatty ketones are those which are prepared by pyrolysis of the magnesium salts of lauric acid, myristic acid, palmitic acid, palmitoleic acid, stearic acid, oleic acid, elaidic acid, petroselic acid, arachidic acid, gadoleic acid, behenic acid or erucic acid.

Further suitable defoamers are fatty acid polyethylene glycol esters, which are preferably obtained by homogeneous base-catalyzed addition reaction of ethylene oxide with fatty acids. In particular, the addition reaction of ethylene oxide with the fatty acids is carried out in the presence of alkanolamines as catalysts. The use of alkanolamines, specifically triethanolamine, leads to an extremely selective ethoxylation of the fatty acids, particularly when the aim is to prepare compounds which have a low degree of ethoxylation. Within the group of fatty acid polyethylene glycol esters, preference is given to those which have a melting point above 25° C., in particular above 40° C.

Within the group of wax-like defoamers, particular preference is given to the paraffin waxes described used alone as wax-like defoamers, or in a mixture with one of the other wax-like defoamers, where the proportion of paraffin waxes in the mixture preferably constitutes more than 50% by weight, based on wax-like defoamer mixture. The paraffin waxes can be applied to supports as required. Suitable carrier materials are all known inorganic and/or organic carrier materials. Examples of typical inorganic carrier materials are alkali metal carbonates, alumosilicates, water-soluble phyllosilicates, alkali metal silicates, alkali metal sulfates, for example sodium sulfate, and alkali metal phosphates. The alkali metal silicates are preferably a compound with an alkali metal oxide to $SiO_2$ molar ratio of from 1:1.5 to 1:3.5. The use of such silicates results in particularly good particle properties, in particular high abrasion stability and nevertheless a high dissolution rate in water. The aluminosilicates referred to as carrier material include, in particular, the zeolites, for example zeolite NaA and NaX. The compounds referred to as water-soluble phyllosilicates include, for example, amorphous or crystalline water glass. In addition, it is possible to use silicates which are available commercially under the name Aerosil® or Sipernat®. Suitable organic carrier materials are, for example, film-forming polymers, for example polyvinyl alcohols, polyvinylpyrrolidones, poly(meth)acrylates, polycarboxylates, cellulose derivatives and starch. Cellulose ethers which can be used are, in particular, alkali metal carboxymethylcellulose, methylcellulose, ethylcellulose, hydroxyethylcellulose and so-called cellulose mixed ethers, such as, for example, methylhydroxyethylcellulose and methylhydroxypropylcellulose, and mixtures thereof. Particularly suitable mixtures are composed of sodium carboxymethylcellulose and methyl-cellulose, where the carboxymethylcellulose usually has a degree of substitution of from 0.5 to 0.8 carboxymethyl groups per anhydroglucose unit and the methylcellulose has a degree of substitution of from 1.2 to 2 methyl groups per anhydroglucose unit. The mixtures preferably comprise alkali metal carboxymethylcellulose and nonionic cellulose ethers in weight ratios of from 80:20 to 40:60, in particular from 75:25 to 50:50. A suitable carrier is also natural starch which is composed of amylose and amylopectin. Natural starch is the term used to describe starch such as is available as an extract from natural sources, for example from rice, potatoes, corn and wheat. Natural starch is a commercially available product and thus readily available. As carrier materials it is possible to use one or more of the compounds mentioned above, in particular chosen from the group of alkali metal carbonates, alkali metal sulfates, alkali metal phosphates, zeolites, water-soluble phyllosilicates, alkali metal silicates, polycarboxylates, cellulose ethers, polyacrylate/polymethacrylate and starch. Particularly suitable mixtures are those of alkali metal carbonates, in particular sodium carbonate, alkali metal silicates, in particular sodium silicate, alkali metal sulfates, in particular sodium sulfate, and zeolites.

Suitable silicones are customary organopolysiloxanes which may have a content of finely divided silica, which in turn may also be silanized. Such organopolysiloxanes are described, for example, in European patent application EP 0496510 A1. Particular preference is given to polydiorganosiloxanes and, in particular, polydimethylsiloxanes which are known from the prior art. Suitable polydiorganosiloxanes have a virtually linear chain and have a degree of oligomerization of from 40 to 1 500. Examples of suitable substituents are methyl, ethyl, propyl, isobutyl, tert-butyl and phenyl. Also suitable are amino-, fatty acid-, alcohol-, polyether-, epoxy-, fluorine-, glycoside- and/or alkyl-modified silicone compounds, which may either be liquid or in resin form at room temperature. Also suitable are simethicones, which are mixtures of dimethicones having an average chain length of from 200 to 300 dimethylsiloxane units and hydrogenated silicates. As a rule, the silicones generally, and the polydiorganosiloxanes in particular, contain finely divided silica, which may also be silanized. For the purposes of the present invention, silica-containing dimethylpolysiloxanes are particularly suitable. The polydiorganosiloxanes advantageously have a Brookfield viscosity at 25° C. (spindle 1, 10 rpm) in the range from 5 000 mPas to 30 000 mPas, in particular from 15 000 to 25 000 mPas. The silicones are preferably used in the form of their aqueous emulsions. The silicone is generally added to an initial charge of water with stirring. If desired, in order to increase the viscosity of the aqueous silicone emulsions, it is possible to add thickeners, as are known from the prior art. These may be inorganic and/or organic in nature, and particular preference is given to nonionic cellulose ethers, such as methylcellulose, ethylcellulose and mixed ethers, such as methylhydroxyethylcellulose, methylhydroxypropylcellulose, methylhydroxybutylcellulose, and anionic carboxycellulose grades, such as carboxymethylcellulose sodium salt (abbreviation CMC). Particularly suitable thickeners are mixtures of CMC to nonionic cellulose ethers in the weight ratio 80:20 to 40:60, in particular 75:25 to 60:40. Usually, and particularly in the case of the addition of the described thickener mixtures, recommended use concentrations are from about 0.5 to 10% by weight, in particular from 2.0 to 6% by weight, calculated as thickener mixture and based on aqueous silicone emulsion. The content of silicones of the type described in the aqueous emulsions is advantageously in the range from 5 to 50 by weight, in particular from 20 to 40% by weight, calculated as silicones and based on aqueous silicone emulsion. According to a further advantageous embodiment, the aqueous silicone solutions receive, as thickener, starch accessible from natural sources, for example from rice, potatoes, corn and wheat. The starch is advantageously present in amounts of from 0.1 up to 50% by weight, based on silicone emulsion and, in particular, in a mixture with the already described thickener mixtures of sodium carboxymethylcellulose and a nonionic cellulose ether in the amounts already given. To prepare the aqueous silicone emulsions, the procedure expediently involves allowing the optionally present thickeners to preswell in water before adding the silicones. The silicones are expediently incorporated using effective stirring and mixing devices.

Disintegrants

The solid preparations can further comprise disintegrants. This term is to be understood as meaning substances which are added to the shaped bodies in order to accelerate their disintegration upon contact with water. Overviews on this subject can be found, for example, in J. Pharm. Sci. 61 (1972), Römpp Chemielexikon, $9^{th}$ Edition, volume 6, p. 4440 and Voigt "Lehrbuch der pharmazeutischen Technologie" [Textbook of Pharmaceutical Technology] ($6^{th}$ Edition, 1987, pp. 182-184). These substances increase in volume upon ingress of water, with on the one hand an increase in the intrinsic volume (swelling) and on the other hand, by way of release of gases as well, the possibility of generating a pressure which causes the tablet to disintegrate into smaller particles. Examples of established disintegration auxiliaries are carbonate/citric acid systems, with the use of other organic acids also being possible. Examples of swelling disintegration auxiliaries are synthetic polymers such as optionally crosslinked polyvinylpyrrolidone (PVP) or natural polymers and/or modified natural substances such as cellulose and starch and their derivatives, alginates or casein derivatives. Preferred disintegrants used for the purposes of the present invention are disintegrants based on cellulose. Pure cellulose has the formal gross composition $(C_6H_{10}O_5)_n$, and, considered formally, is a β-1,4-polyacetal of cellobiose, which itself is constructed from two molecules of glucose. Suitable celluloses consist of about 500 to 5 000 glucose units and, accordingly, have average molar masses of from 50 000 to 500 000. Cellulose-based disintegrants which can be used for the purposes of the present invention are also cellulose derivatives obtainable by polymer-analogous reactions from cellulose. Such chemically modified celluloses include, for example, products of esterifications and etherifications in which hydroxyl hydrogen atoms have been substituted. However, celluloses in which the hydroxyl groups have been replaced by functional groups not attached via an oxygen atom may also be used as cellulose derivatives. The group of cellulose derivatives includes, for example, alkali metal celluloses, carboxymethylcellulose (CMC), cellulose esters and ethers and also aminocelluloses. Said cellulose derivatives are preferably not used alone as cellulose-based disintegrants, but instead are used in a mixture with cellulose. The cellulose derivative content of these mixtures is preferably less than 50% by weight, particularly preferably less than 20% by weight, based on the cellulose-based disintegrant. A particularly preferred cellulose-based disintegrant used is pure cellulose which is free from cellulose derivatives. A further cellulose-based disintegrant, or constituent of this component, which may be used is microcrystalline cellulose. This microcrystalline cellulose is obtained by partial hydrolysis of celluloses under conditions which attack only the amorphous regions (approximately 30% of the total cellulose mass) of the celluloses and break them up completely, but leave the crystalline regions (about 70%) intact. Subsequent deaggregation of the microfine celluloses resulting from the hydrolysis yields the microcrystalline celluloses, which have primary particle sizes of approximately 5 μm and can be compacted, for example, to give granulates having an average particle size of 200 μm. The disintegrants can, viewed macroscopically, be homogeneously distributed within the shaped body, but, viewed microscopically, form zones of increased concentration as a result of the preparation. Disintegrants which may be present for the purposes of the invention, such as, for example, kollidon, alginic acid and alkali metal salts thereof, amorphous and also partially crystalline phyllosilicates (bentonites), polyacrylates, polyethylene glycols are given, for example, in the printed specifications WO 98/40462 (Rettenmaier), WO 98/55583 and WO 98/55590 (Unilever) and WO 98/40463, DE 19709991 and DE 19710254 A1 (Henkel). Reference is expressly made to the teaching of these specifications. The shaped bodies can comprise the disintegrants in amounts of from 0.1 to 25% by weight, preferably 1 to 20% by weight and in particular 5 to 15% by weight, based on the shaped bodies.

Fragrances

Perfume oils or fragrances which can be used are individual fragrance compounds, e.g. the synthetic products of the ester, ether, aldehyde, ketone, alcohol and hydrocarbon type. Fragrance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethyl methylphenylglycinate, allyl cyclohexylpropionate, styrallyl propionate and benzyl salicylate. The ethers include, for example, benzyl ethyl ether; the aldehydes include, for example, the linear alkanals having 8-18 carbon atoms, citral, citronellal, citronellyloxy-acetaldehyde, cyclamen aldehyde, hydroxycitronellal, lilial and bourgeonal; the ketones include, for example, the ionones, α-isomethylionone and methyl cedryl ketone; the alcohols include anethole, citronellol, eugenol, geraniol, linalool, phenylethyl alcohol and terpineol; the hydrocarbons include mainly the terpenes, such as limonene and pinene. Preference is, however, given to using mixtures of different fragrances which together produce a pleasing fragrance note. Such perfume oils can also comprise natural fragrance mixtures, is such as are obtainable from vegetable sources, e.g. pine oil, citrus oil, jasmine oil, patchouli oil, rose oil or ylang-ylang oil. Likewise suitable are muscatel, sage oil, camomile oil, oil of cloves, melissa oil, mint oil, cinnamon leaf oil, linden blossom oil, juniper berry oil, vetiver oil, olibanum oil, galbanum oil and labdanum oil, and orange blossom oil, neroli oil, orange peel oil and sandalwood oil.

The fragrances can be incorporated directly into the compositions according to the invention, although it may also be advantageous to apply the fragrances to carriers which enhance the adhesion of the perfume to the laundry and, as a result of a slower release of fragrance, ensure long-lasting fragrance of the textiles. Cyclodextrins have, for example, proven successful as such carrier materials, where the cyclodextrin-perfume complexes can also additionally be coated with further auxiliaries.

Inorganic Salts

Further suitable ingredients of the compositions are water-soluble inorganic salts, such as bicarbonates, carbonates, amorphous silicates, normal waterglasses, which do not have outstanding builder properties, or mixtures thereof; in particular, alkali metal carbonate and/or amorphous alkali metal silicate, primarily sodium silicate with a molar ratio of $Na_2O$:$SiO_2$ of 1:1 to 1:4.5, preferably from 1:2 to 1:3.5, are used. The content of sodium carbonate in the end preparations is here preferably up to 40% by weight, advantageously between 2 and 35% by weight. The content in the compositions of sodium silicate (without particular builder properties) is generally up to 10% by weight and preferably between 1 and 8% by weight. Fillers and extenders which may be present are also, for example, sodium sulfate in amounts of from 0 to 10% by weight, in particular 1 to 5% by weight, based on the compositions.

EXAMPLES

Example P1

In a 3-l three-neck flask fitted with stirrer, distillation attachment and vacuum connection, 1 000 g (1.52 mol) of hydrogenated coconut oil, 720 g (4.45 mol) of aminopropylmethylethanolamine (APMMEA) and 7 g of hypophosphoric acid were mixed at 85° C. The mixture was heated to 180° C. and stirred at this temperature for 5 h, during which the water of condensation was continuously distilled off. Finally, the pressure was reduced to 10 mbar in order to remove unreacted amine. Then, in a second reaction vessel, 230 g (1.97 mol) of sodium chloroacetate were dissolved in 670 ml of water at 85° C. To this solution were added, in portions, 550 g (1.78 mol) of the amidoamine prepared previously, the pH being maintained between 6 and 9. The mixture was then heated to 90° C. and stirred at this temperature for 5 h, where, toward the end of the reaction, sodium hydroxide was added in order to keep the pH constant. The betaine was obtained as a yellowish-transparent liquid which had a dry residue of 51.3% by weight. The active substance content was 44.0% by weight, the content of NaCl was 7.7% by weight.

Example P2

Analogously to Example P1, 632 g (2.05 mol) of the amidoamine obtained as intermediate were dissolved in 98 g of isopropyl alcohol at 60° C. Then, 245 g (1.94 mol) of dimethyl sulfate were added to the mixture in portions with stirring, during which the temperature was maintained between 60 and 70° C. over 4 h. The amide quat was obtained as a viscous liquid with an active substance content of 90% by weight.

The table below gives a number of formulation examples.

TABLE 1

Cosmetic preparations (water, preservatives add to 100% by weight)

| | Composition (INCI) | | | | | | | | | |
|---|---|---|---|---|---|---|---|---|---|---|
| | 1 | 2 | 3 | 4 | 5 | 6 | 7 | 8 | 9 | 10 |
| Texapon ® NSO<br>Sodium Laureth Sulfate | — | — | — | — | — | — | 38.0 | 38.0 | 25.0 | — |
| Texapon ® SB 3<br>Disodium Laureth Sulfosuccinate | — | — | — | — | — | — | — | — | 10.0 | — |
| Plantacare ® 818<br>Coco Glucosides | — | — | — | — | — | — | 7.0 | 7.0 | 6.0 | — |

TABLE 1-continued

Cosmetic preparations (water, preservatives add to 100% by weight)

| | Composition (INCI) | | | | | | | | | |
|---|---|---|---|---|---|---|---|---|---|---|
| | 1 | 2 | 3 | 4 | 5 | 6 | 7 | 8 | 9 | 10 |
| Plantacare ® PS 10<br>Sodium Laureth Sulfate (and) Coco Glucosides | — | — | — | — | — | — | — | — | — | 10.0 |
| Betaine as in Ex. P1 | — | — | — | — | — | — | 5.0 | 5.0 | 10.0 | 4.0 |
| Amide quat as in Example P2 | 2.0 | 2.0 | 2.0 | 2.0 | 4.0 | 4.0 | — | — | — | — |
| Eumulgin ® B2<br>Ceteareth-20 | 0.8 | 0.8 | — | 0.8 | — | 1.0 | — | — | — | — |
| Eumulgin ® VL 75<br>Lauryl Glucoside (and) Polyglyceryl-2 Polyhydroxystearate (and) Glycerin | — | — | 0.8 | — | 0.8 | — | — | — | — | — |
| Lanette ® OB<br>Cetearyl Alcohol | 2.5 | 2.5 | 2.5 | 2.5 | 3.0 | 2.5 | — | — | — | — |
| Cutina ® GMS<br>Glyceryl Stearate | 0.5 | 0.5 | 0.5 | 0.5 | 0.5 | 1.0 | — | — | — | — |
| Cetiol ® HE<br>PEG 7 Glyceryl Cocoate | 1.0 | — | — | — | — | — | — | — | 1.0 | — |
| Cetiol ® PGL<br>Hexyldecanol (and) Hexyldecyl Laurate | — | 1.0 | — | — | 1.0 | — | — | — | — | — |
| Cetiol ® V<br>Decyl Oleate | — | — | — | 1.0 | — | — | — | — | — | — |
| Eutanol ® G<br>Octyldodecanol | — | — | 1.0 | — | — | 1.0 | — | — | — | — |
| Nutrilan ® Keratin W<br>Hydrolyzed Keratin | — | — | — | 2.0 | — | — | — | — | — | — |
| Lamesoft ® LMG<br>Glyceryl Laurate (and) Potassium Cocoyl Hydrolyzed Collagen | — | — | — | — | — | — | 3.0 | 2.0 | 4.0 | — |
| Euperlan ® PK 3000 AM<br>Glycol Distearate (and) Laureth-4 (and) Cocamidopropyl Betaine | — | — | — | — | — | — | — | 3.0 | 5.0 | 5.0 |
| Generol ® 122 N<br>Soya sterol | — | — | — | — | 1.0 | 1.0 | — | — | — | — |
| Highcareen ® GS<br>Betaglucan | 1.0 | 1.0 | 1.0 | 1.0 | 1.0 | 1.0 | 1.0 | 1.0 | 1.0 | 1.0 |
| Hydagen ® CMF<br>Chitosan | 1.0 | 1.0 | 1.0 | 1.0 | 1.0 | 1.0 | 1.0 | 1.0 | 1.0 | 1.0 |
| Copherol ® 12250<br>Tocopherol Acetate | — | — | 0.1 | 0.1 | — | — | — | — | — | — |
| Arlypon ® F<br>Laureth-2 | — | — | — | — | — | — | 3.0 | 3.0 | 1.0 | — |
| Sodium Chloride | — | — | — | — | — | — | — | 1.5 | — | 1.5 |

(1-4) hair rinse,
(5-6) hair treatment,
(7-8) shower preparation,
(9) shower gel,
(10) washing lotion

What is claimed is:

1. A surfactant concentrate consisting of:
   (a) greater than 50% by weight of one or more quaternary surfactants of formula (I),

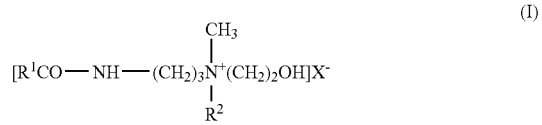

(I)

wherein $R^1CO$ is a linear, saturated, optionally hydroxy-functionalized acyl moiety having 6 to 22 carbon atoms, $R^2$ is $C_{1-4}$ alkyl, $CH_2CH_2OH$ or $CH_2CH_2OCH_2CH_2OH$, and X is halide, alkyl sulfate, alkyl carbonate or alkyl phosphate; and
   (b) water,
   and wherein said concentrate is flowable and/or pumpable, with a Brookfield viscosity of less than 10000 mPas.

2. The surfactant concentrate of claim 1 wherein $R^2$ in said quaternary surfactant of the formula (I) is a C1-C4 alkyl group.

3. The surfactant concentrate of claim 1 wherein $R^2$ in said quaternary surfactant of the formula (I) is $CH_2CH_2OH$ or $CH_2CH_2OCH_2CH_2OH$.

4. A cosmetic or pharmaceutical preparation comprising the surfactant concentrate of claim 1.

5. The surfactant concentrate of claim 1 wherein $R^1CO$ in said quaternary surfactant of formula (I) comprises hydrogenated coconut fatty acid moieties.

6. The surfactant concentrate of claim 1 wherein said concentrate is transparent and remains transparent even upon prolonged storage at elevated temperature.

7. A surfactant concentrate consisting of:
   (a) greater than 50% by weight of one or more quaternary surfactants of formula (I),

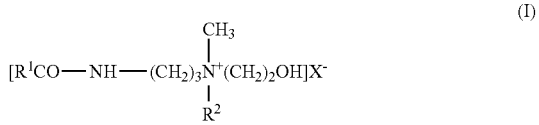

(I)

wherein $R^1CO$ is a linear, saturated, optionally hydroxy-functionalized acyl moiety having 6 to 22 carbon atoms, $R^2$ is $C_{1-4}$ alkyl, $CH_2CH_2OH$ or $CH_2CH_2OCH_2CH_2OH$, and X is halide, alkyl sulfate, alkyl carbonate or alkyl phosphate; and
  (b) aqueous alcohol,
    wherein the alcohol is selected from the group consisting of ethanol, isopropanol, and propylene glycol,
    and wherein said concentrate is flowable and/or pumpable, with a Brookfield viscosity of less than 10000 mPas.

8. The surfactant concentrate of claim 7, wherein said alcohol is ethanol.

9. The surfactant concentrate of claim 7, wherein said alcohol is isopropanol.

10. The surfactant concentrate of claim 7 wherein $R^2$ in said quaternary surfactant of the formula (I) is a C1-C4 alkyl group.

11. The surfactant concentrate of claim 7 wherein $R^2$ in said quaternary surfactant of the formula (I) is $CH_2CH_2OH$ or $CH_2CH_2OCH_2CH_2OH$.

12. A cosmetic or pharmaceutical preparation comprising the surfactant concentrate of claim 7.

13. The surfactant concentrate of claim 7 wherein $R^1CO$ in said quaternary surfactant of formula (I) comprises hydrogenated coconut fatty acid moieties.

14. The surfactant concentrate of claim 7 wherein said concentrate is transparent and remains transparent even upon prolonged storage at elevated temperature.

* * * * *